United States Patent [19]

Dishman

[11] Patent Number: 4,929,885

[45] Date of Patent: May 29, 1990

[54] APPARATUS FOR MEASURING GROUND MOISTURE CONTENT OF SOIL

[75] Inventor: Michael R. Dishman, Raleigh, N.C.

[73] Assignee: Troxler Electronic Laboratories, Inc., Research Triangle Park, N.C.

[21] Appl. No.: 268,935

[22] Filed: Nov. 8, 1988

[51] Int. Cl.$^5$ .............................................. G01R 27/26
[52] U.S. Cl. .................................... 324/664; 324/690
[58] Field of Search ...................... 324/61 R, 61 P, 65, 324/71.2; 73/73; 340/602; 361/178; 239/63; 137/392

[56] References Cited

U.S. PATENT DOCUMENTS

| | | | |
|---|---|---|---|
| 2,266,114 | 12/1941 | Bartlett | 324/61 P |
| 2,729,099 | 1/1956 | Rosenthal | 73/73 |
| 2,793,527 | 5/1957 | Turner, Jr. et al. | 73/73 |
| 2,941,174 | 6/1960 | Richards | 338/35 |
| 3,155,899 | 11/1964 | Davidson | 324/61 R |
| 3,155,900 | 11/1964 | Hanken | 324/61 R |
| 3,155,902 | 11/1964 | Walls | 324/61 R |
| 3,253,458 | 5/1966 | Katz et al. | 73/73 |
| 3,486,996 | 12/1969 | Annand | 324/71.2 X |
| 3,546,928 | 12/1970 | Ivarsson | 324/61 R |
| 4,039,939 | 8/1977 | Wagner | 324/57 Q |
| 4,044,607 | 8/1977 | Deal | 324/61 R X |
| 4,168,465 | 9/1979 | Prince | 324/61 P |
| 4,245,188 | 1/1981 | Rottmar | 324/61 P |
| 4,259,632 | 3/1981 | Ahtiainen | 324/61 R |
| 4,399,404 | 8/1983 | Resh | 324/61 R |
| 4,408,481 | 10/1983 | Sidey | 73/73 |
| 4,445,788 | 5/1984 | Twersky et al. | 73/73 X |
| 4,453,401 | 6/1984 | Sidey | 73/73 |
| 4,499,111 | 2/1985 | Oetiker et al. | 324/61 R X |
| 4,549,245 | 10/1985 | Fleckenstein | 324/61 P X |
| 4,752,727 | 6/1988 | Schneider | 324/61 P |

OTHER PUBLICATIONS

In Situ Measurement of Moisture in Soil and Similar Substances by Fringe Capacitance–by A. M. Thomas–J. Sci. Instrum., vol. 43, 1966, pp. 21–27.
Testing of a Field Dielectric Soil Moisture Meter–by Vaclav Kuraz–Geotechnical Testing Journal, GTJODJ, vol. 4, No. 3, Sep. 1981, pp. 111–116.
A Frequency Shift Dielectric Soil Moisture Sensor–by D. Wobschall–IEEE Transactions on Geoscience Electronics, vol. GE-16, No. 2, Apr. 1978, pp. 112–118.
Resonsance Capacitance Soil Moisture Meter–by V. Kuraz et al–Soil Science, vol. 110, No. 4, 1970, pp. 278–279.
Relationship of Soil Moisture to the Dielectric Property, by E. T. Selig and S. Mansukhani; Journal of the Geotechnical Engineering Division, Proceedings of the American Society of Civil Engineers, vol. 101, No. GT8, Aug. 1975.
Instrumentation for Moisture Measurement–Bases, Subgrades, and Earth Materials (Sensor Evaluation), by G. A. Matzkanin, E. T. Selig and D. C. Wobschall; NCHRP Final Report SwRI Project No. 15-4063, Dec. 1979.
The Design of an Electrical Capacitance-Type Moisture Meter for Agricultural Use, by J. Matthews; Journal of Agricultural Engineering Research, vol. 8, No. 1, pp. 17–30, 1963.
High Dielectric Constant Microwave Probes for Sensing Soil Moisture, by J. R. Birchak, C. G. Gardner, J. E. Hipp and J. M. Victor; Proceedings of the IEEE, vol. 62, No. 1, Jan. 1974.

*Primary Examiner*—Reinhard J. Eisenzopf
*Assistant Examiner*—Jack B. Harvey
*Attorney, Agent, or Firm*—Bell, Seltzer, Park & Gibson

[57] ABSTRACT

A method of measuring the moisture content of soil wherein a tapered probe is inserted into a tapered hole formed in the ground. The walls of the hole are tapered substantially in correspondence with the taper of the probe and such that the soil adjacent the walls is not compacted or otherwise affected. In this manner, good contact between the surface of the probe and the soil is obtained. The probe is a capacitance sensing probe with a pair of spaced electrodes along the tapered surface with a dielectric material in between. The electrodes serve as structural members of the probe body and the hollow internal portion is backfilled to prevent moisture from permeating the probe.

6 Claims, 1 Drawing Sheet

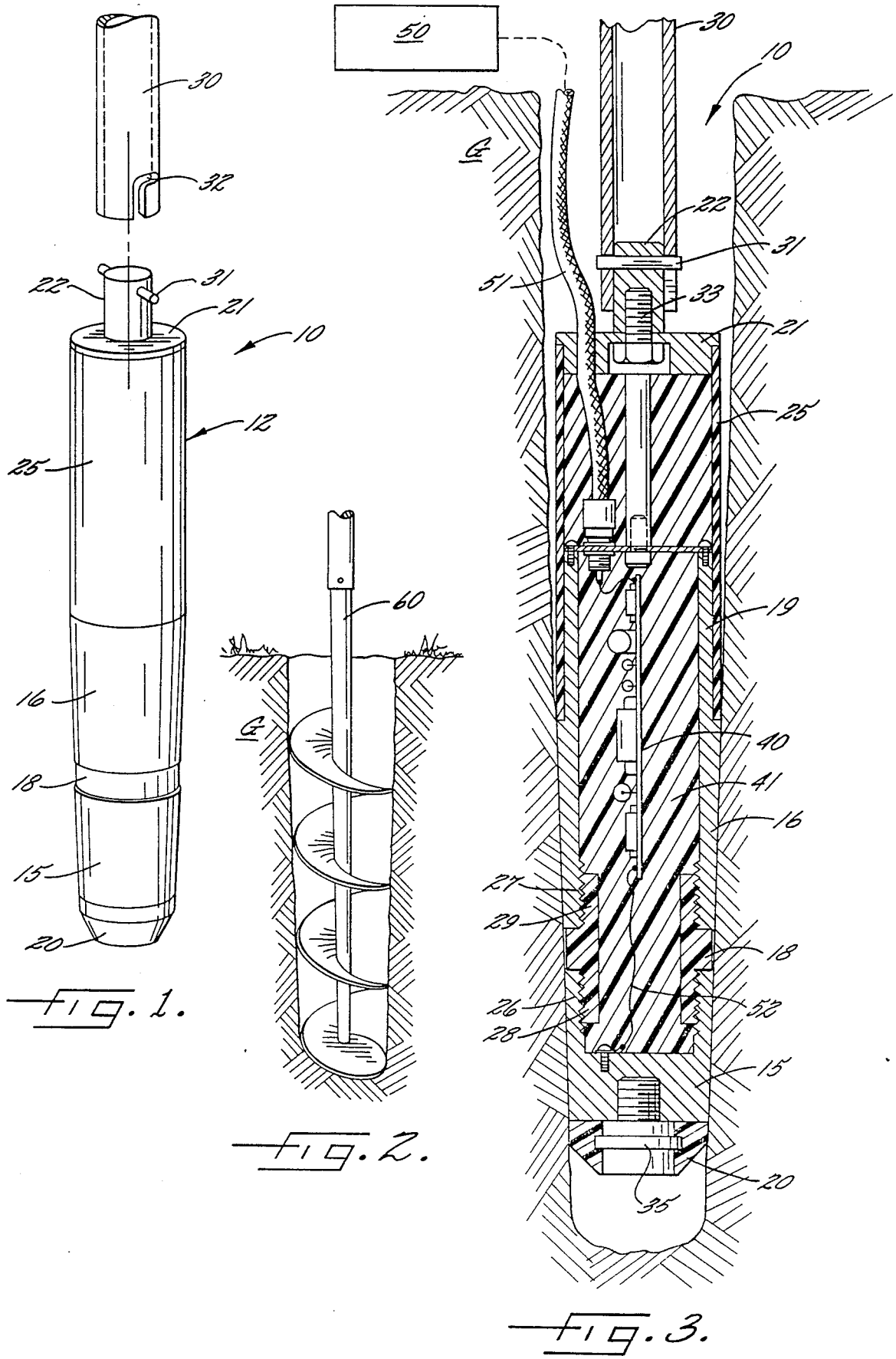

APPARATUS FOR MEASURING GROUND MOISTURE CONTENT OF SOIL

FIELD OF THE INVENTION

This invention is directed to a method and apparatus of determining the ground moisture content of soil and more particularly to a method and apparatus for providing improved contact between uncompacted ground soil and the electrodes of a capacitance moisture sensing probe.

BACKGROUND OF THE INVENTION

It is well known to provide supplemental irrigation systems to assure that crops and other vegetation are provided with adequate water. This is especially important during times of little or irregular rainfall. It is important, however, to use the precious water resource efficiently and not to irrigate when it is unnecessary. As such, it is known to test soil conditions to determine moisture content. An approximate indication of soil moisture content can be readily obtained by simply observing the appearance and the consistency of the soil. If a more accurate, quantitative measurement is required, a common method of determining moisture content of soil is to obtain a soil sample and weigh it before and after oven drying. The sample is heated and dried to eliminate all moisture and the weight difference before and after represents the moisture in the soil. This method is slow and time consuming and is not very suitable for determining changing moisture content.

It is also known to determine the moisture content of soil by providing moisture sensing probes embedded in the soil. For example, U.S. Pat. No. 4,445,788 to Twersky et al shows a device for determining the moisture content, temperature and root development of soil. The device has helical threads at a lower end and several sensing stations along an outer tapered surface. The sensing stations include a camera and liquid crystals to transmit images to a viewing station above the surface through a series of fiber optic wires. A drawback of Twersky et al, in addition to its complexity, is that by driving the device down into the earth with the helical threads, the soil is compressed, which alters the amount of absorbed moisture in the soil and thus gives an inaccurate indication of soil moisture content.

Another type of moisture probe is a capacitance test probe such as shown by A. M. Thomas, "In Situ Measurement of Moisture in Soil and Similar Substances by Fringe Capacitance", *J. Sci. Instrum.*, Vol. 43, 1966, pp. 21-27. The probe is square in cross section and includes two wedge shaped electrodes positioned on a pointed end of the probe. The probe is pushed down into the soil to measure the moisture content. However, pushing the probe down into the soil disturbs the soil and, as discussed above, impairs the accuracy of the measurement.

Other capacitance moisture probes have been proposed, such as Kuraz, "Testing of a Field Dielectric Soil Moisture Meter," *Geotechnical Testing Journal,* GTJODJ, Vol. 4, No. 3, September 1981, pp. 111-116, Wobschall, "A Frequency Shift Dielectric Soil Moisture Sensor," *IEEE Transactions on Geoscience Electronics,* Vol. GE-16, No. 2, April 1978, pp. 112-118 and Kuraz et al, "Resonance-Capacitance Soil Moisture Meter," *Soil Science,* Vol. 110, No. 4, 1970, pp. 278-279. These probes, however, are not designed to provide uniform contact with undisturbed soil.

Capacitance probes have also been used to measure the moisture content of materials other than soil. For example, U.S. Pat. No. 4,044,607 to Deal and U.S. Pat. No. 4,399,404 to Resh disclose capacitance moisture sensing devices used for grain storage units. These types of probes however are unsuitable for measuring the moisture content of soil because of the intrinsic differences between ground soil and stored grain. Grain is fairly light in weight and does not compact like soil. Therefore, a probe may be pushed and rocked down into the grain unit and the grain will flow in, around, and with the probe to maintain contact with the probe on all sides. However, driving a probe down into soil will compact the soil and alter the amount of absorbed moisture therein. Also, when the soil is compacted, it generally retains the compacted shape. Therefore, if the probe is rocked into place, the probe will not be in proper uniform contact with the soil to obtain an accurate measurement.

Accordingly, it is an object of the present invention to provide a method of determining the moisture content of soil which avoids the aforementioned drawbacks of the prior art.

It is a more particular object of the present invention to provide a method of determining the moisture content of soil which provides a more reliable and more accurate measurement and which is simple and efficient.

It is also an object of the present invention to provide a durable capacitance moisture sensing probe having the electrodes along the tapered outer surface portion to provide easier and reliable contact with the soil.

SUMMARY OF THE INVENTION

The above and other objects of the invention have been achieved in accordance with the present invention by a method and means which ensures establishing firm contact between a probe and uncompacted soil. In accordance with the present invention a hole is formed in the soil having tapered walls to receive a probe with a corresponding taper. More specifically, the tapered hole is formed by selectively withdrawing soil from the ground to form a hole having walls with a predetermined taper from the axis of the hole. A moisture probe having a tapered surface corresponding substantially to the predetermined taper of the hole is then inserted into the tapered hole. The probe is moved axially until the tapered surface of the probe is positioned in firm soil contacting relationship with the walls of the hole, and then the ground moisture content of the soil in contact with the probe is measured. This method achieves accurate and reproducible results by assuring firm contact of the probe with the soil without disturbing or compacting the soil.

In a preferred embodiment, the probe used to measure the ground moisture content of soil comprises a generally cylindrical body having first and second opposite ends and a tapered surface portion along the body between said first and second ends which tapers down in the direction from said second end to said first end. The probe further includes means defining a first electrode at a first location along said tapered body surface portion and means defining a second electrode at a second location longitudinally spaced from said first electrode. A dielectric extends between the first and second electrodes for dielectrically separating the electrodes so that the probe senses the capacitance across the first and second electrodes. A measurement of the capacitance of the soil in the vicinity of the electrodes is used to determine the moisture content of the soil.

BRIEF DESCRIPTION OF THE DRAWINGS

Some of the features and advantages of the invention have been stated, and others will become apparent as the description of the invention proceeds, taken in conjunction with the accompanying drawings, in which FIG. 1 is a perspective view of a preferred embodiment of the tapered capacitance moisture sensing probe of the present invention;

FIG. 2 is a cross section view showing how a tapered hole is formed in the ground using a tapered auger; and FIG. 3 is an enlarged cross section view of the tapered capacitance moisture sensing probe.

DESCRIPTION OF THE PREFERRED EMBODIMENT

In accordance with the present invention, an accurate measurement of the moisture content of soil is best obtained by providing a moisture measuring probe in firm soil contact with undisturbed soil. Such contact is obtained by forming a hole having a tapered configuration for receiving a similarly configured tapered probe which may be easily inserted and removed from the hole. The hole must also be formed so as not to disturb the soil along the walls of the hole. More particularly, referring to FIG. 2, a hole having tapered walls is formed by selectively removing soil from the ground G. By selectively removing the soil to form the hole rather than forcing or driving a rod or other hole forming element into the soil, the soil in the vicinity of the walls of the hole is not compacted. In the preferred embodiment, the hole is formed by a tapered auger 60 which bores holes of consistent size with a predetermined taper. The auger 60 also minimally disturbs the soil at the side walls.

Once the hole is properly formed, a probe having a tapered surface substantially corresponding to the tapered walls of the hole is inserted into the hole to measure the moisture content of the soil. Once the probe is in the hole, it is moved axially into firm soil contacting relationship with the walls of the hole so that the tapered outer surface of the probe is in snug contact. The use of a tapered probe in a tapered hole also provides generally uniform contact without having to excessively force the probe and thereby compact the soil. The probe then may take an accurate measurement of the moisture content of the soil in the proximity of the probe. It should be noted that the moisture probe may employ any of a variety of known methods of measuring the moisture content of the soil such as measuring the resistance or capacitance of the soil. In the preferred embodiment, the capacitance of the soil is used to determine the moisture content of soil.

It is important that the soil at the walls not be compacted or substantially disturbed. Compacting the soil may alter the amount of absorbed moisture and cause an inaccurate measurement. If the soil is disturbed to the extent that there are air pockets or voids in the vicinity of the probe, such as if soil is removed and replaced to bury the probe, inaccuracies will also occur. To effect minimum disturbance of the soil, it is desirable that the angle of the taper with respect to the longitudinal axis be relatively small. According to the present invention, the angle should preferably be in the range of 0.5 to about 5 degrees, with the most desired angle being about 1.5 degrees. This angle insures that the forces exerted on the soil when digging the hole are nearly perpendicular to the walls of the hole rather than outwardly so that the compressive force is received almost entirely by the soil at the bottom of the hole. In contrast, if the angle is much greater, the walls may receive substantial outward compressive forces.

Once the measurement is taken, the probe is normally removed from the ground so that a measurement may be taken at another location or at another depth. However, it is within the scope of the present invention to leave the probe in the ground so that subsequent measurements may be taken at the same location over an extended period of time.

The preferred embodiment of the capacitance moisture sensing probe used in the above process is best illustrated in FIGS. 1 and 3. The capacitance moisture sensing probe, generally indicated by reference numeral 10, comprises a generally cylindrical elongate body 12 which has a slight taper. Preferably, the angle of the taper ranges from 0.5 to 5 degrees from the axis of the probe, but is 1.5 degrees in the preferred embodiment. The body 12 includes first and second electrodes 15 and 16 and a dielectric spacer 18. The first and second electrodes 15 and 16 are formed as rigid load bearing structural components in the shape of generally circumferential cylindrical sleeves. The outer surface portion of the probe is slightly tapered so the second electrode 16 has a slightly larger diameter than the first electrode 15. Therefore, as the probe body is inserted into the ground, as best illustrated in FIG. 3, each of the electrodes 15 and 16 makes firm contact with the ground. Preferably, the electrodes are made of stainless steel to provide good electrical conductivity and resistance to abrasion and corrosion. Alternatively, the probe may be manufactured with more than two electrodes. For example, the probe may have a number of pairs of electrodes along an extended probe body to measure the moisture content at several depths simultaneously.

The dielectric spacer 18 is formed as a cylindrical dielectric sleeve and is positioned between the first and second electrodes 15 and 16 to dielectrically space one from the other. The spacer 18 has threaded opposite end portions 28 and 29 which are arranged to respectively engage the threaded end portions 26 and 27 of the first and second electrodes. The spacer 18 also includes an outer surface portion which is shown to be cylindrical. The outer surface portion may alternatively be tapered to form a smoothly tapered outer surface portion of the body 12. The spacer 18 may be formed of polypropylene plastic or other suitable dielectric material.

An insulating tip 20 is attached to a first end of the body 12 by a sCreW 35 received into the first electrode 15. The insulating tip 20 should be a resilient material and preferably non-conductive. The tip 20 spaces the probe, and particularly the electrodes, off the bottom of the hole so that the measurement is obtained from the soil in the proximity of the electrodes along the walls of the hole. The tip 20 also provides protection for the probe so that as the probe is inserted into and removed from the ground, any hard objects such as rocks or roots etc. do not damage the probe itself.

In the illustrated embodiment, the upper portion of the probe is formed by tubular sleeve 25 attached to the upper end of the second electrode 16 by an adhesive or other means. The tubular sleeve 25 may also be tapered like the electrodes but is preferably cylindrical so as not to interfere with the electrodes making good contact with the soil. As such, the body 12 has a portion of the outer surface which is tapered and the remainder is cylindrical. The tubular portion 25 is preferably formed of a resilient dielectric material such as fiberglass. An end cap 21 is attached to the second end of the body which is the upper end of the tubular sleeve 25 by an adhesive or other means. The end cap 21 includes a insertion-extraction post 22 attached to the end cap 21 by a screw 33 or other conventional means. A tool 30 which attaches to insertion-extraction post 22 may be used to facilitate handling of the probe below the ground surface. The tool may be removably attached by any conventional means such as the illustrated bayonet connection using pins 31 and slots 32.

In accordance with the preferred embodiment of the present invention, the moisture content of the soil is determined by measuring the capacitance of the soil. The dielectric constant for most soils is between 2 and 4. Water, however, has a dielectric constant of approximately 78 to 81 depending on the temperature. Therefore, the capacitance of the soil provides a good indication of the moisture content of the soil.

The capacitance moisture sensor probe 10 is provided with an LC circuit which includes the first electrode 15, electrical connection wire 52, circuit board 40, coaxial connection wire 51, control box 50, and second electrode 16. The circuit is completed by providing the electrodes 15 and 16 in firm contact with the soil. The circuit board 40 includes an oscillator having a particular resonant frequency in the range of 50 MHz. A change in the capacitance of the soil in the proximity of the electrodes causes a shift of the resonant frequency which can be easily measured by the control box 50. The probe electrodes 15 and 16 are periodically briefly switched out of the circuit by means of switching circuitry on the circuit board 40 during which time a reference frequency is determined, and the frequency shift is measured relative to this reference frequency. The control box 50 provides an indication of the moisture content of the soil to the user by correlating the capacitance of the soil to the moisture content of the soil. The correlation is developed by successively measuring various known test samples and recording the measured capacitances. The data may then be correlated by any known method such as a mathematical formula or simply by maintaining an array of the various capacitances cross referenced with the appropriate moisture contents.

A particular feature of the present invention is the moisture impermeability of the internal cavity formed within the body 12. To seal the cavity, the spacer 18 is tightly coupled to the electrodes 15 and 16 by threaded end portions which sealingly resist penetration of water. The tubular portion 20 is sealed to the second electrode 16 over the extended shoulder portion 19 and the top cap 21 is sealed to the tubular portion 20. To further assure that the cavity is sealed, the internal cavity is backfilled with a dielectric filler 41 such as hot melt glue. The dielectric filler 41 also fixes the circuit board 40 and the wires 51 and 52 in place and provides a further moisture barrier against corroding or damaging the circuit board 40. The hot melt glue is comprised of a low dielectric thermoplastic resin such as Jet-Melt Adhesive 3738 manufactured by 3M Corp.

In an alternative embodiment according to the present invention, the probe includes a thin protective coating. For example, the probe may have a thin coating of ceramic or plastic or other non-conductive material to provide a smooth outer surface that will resist the scratches and abrasions the probe receives without affecting the accuracy of the measurements.

The foregoing description is to be considered illustrative rather than restrictive of the invention, and those modifications which come within the meaning and range of equivalence of the claims are to be included therein.

That which is claimed:

1. A capacitance moisture sensor probe for sensing the ground moisture content of soil, the moisture sensor probe having a generally cylindrical body with first and second opposite ends, the generally cylindrical body comprising:

a first substantially rigid structural component having a tapered outer surface portion defining a first electrically conductive capacitance sensing electrode;

a second substantially rigid structural component having a tapered outer surface portion defining a second electrically conductive capacitance sensing electrode;

a dielectric spacer securely attached to each of said first and second components such that said components are dielectrically and longitudinally spaced apart at opposite ends of said spacer so that the moisture sensor probe senses the capacitance of soil in the proximity of the first and second electrodes and wherein said dielectric spacer includes threaded opposite end portions, and each said first and second structural components have threaded end portions cooperating with said threaded end portions of said dielectric spacer to secure the first and second structural components to the dielectric spacer; and wherein one of said components has an internal cavity and said body includes an electronic circuit located within said internal cavity and electrically connected to each of said first and second electrodes, and said internal cavity further including a dielectric filler surrounding the electronic circuit and filling said internal cavity to prevent water from permeating the internal cavity and harming the electronic circuit.

2. The moisture sensor probe according to claim 1 further comprising an insulating tip attached to said first component and located at said first end of said body.

3. The moisture sensor probe according to claim 1 wherein said body further includes an end cap located at said second end of the body and an insertion-extraction post attached to and extending from said end cap.

4. The moisture sensor probe according to claim 3 further including a dielectric cylindrical tube portion having opposite ends, a first end being attached to said second structural component and the other end being attached to said end cap.

5. The moisture sensor probe according to claim 1 wherein said dielectric spacer has a tapered outer surface portion and the tapered outer surface portions of the dielectric spacer and the first and second structural elements form a generally continuous smooth tapered outer surface.

6. A capacitance moisture sensor probe for sensing the ground moisture content of soil, the moisture sensor probe having a generally cylindrical body with first and second opposite ends, the generally cylindrical body comprising:

a first substantially rigid structural component having a tapered outer surface portion defining a first electrode and a threaded end portion;

a second substantially rigid structural component having a tapered outer surface portion defining a second electrode and a threaded end portion;

a dielectric spacer having an outer surface portion and opposite threaded end portions securely attached to said threaded end portions of each of said first and second components such that said components are dielectrically and longitudinally spaced apart at opposite ends of said spacer by said outer surface portion of said spacer and so that the moisture sensor probe senses the capacitance of soil in the proximity of the first and second electrodes;

an insulating tip attached to said first component and located at said first end of said body;

wherein at least one of said components has an internal cavity and said body includes an electronic circuit located within said internal cavity and electrically connected to each of said first and second electrodes, and said internal cavity further including a dielectric filler surrounding the electronic circuit and filling said internal cavity to prevent water from permeating the internal cavity and harming the electronic circuit;

an end cap located at said second end of said body with an insertion-extraction post attached to and extending from said end cap; and a dielectric cylindrical tube portion having opposite ends, wherein a first end is attached to said second structural component and the other end is attached to said end cap.

* * * * *